United States Patent
Guilford

(10) Patent No.: US 9,777,006 B2
(45) Date of Patent: Oct. 3, 2017

(54) INHIBITORS OF LEUKOTRIENE A4 HYDROLASE

(71) Applicant: Celtaxsys, Inc., Atlanta, GA (US)

(72) Inventor: William Guilford, Belmont, CA (US)

(73) Assignee: Celtaxsys, Inc., Atlanta, GA (US)

( * ) Notice: Subject to any disclaimer, the term of this patent is extended or adjusted under 35 U.S.C. 154(b) by 0 days.

(21) Appl. No.: 14/849,825

(22) Filed: Sep. 10, 2015

(65) Prior Publication Data

US 2016/0068534 A1    Mar. 10, 2016

Related U.S. Application Data

(63) Continuation of application No. PCT/US2014/027428, filed on Mar. 14, 2014.

(60) Provisional application No. 61/781,193, filed on Mar. 14, 2013.

(51) Int. Cl.
*A61K 31/519* (2006.01)
*C07D 487/04* (2006.01)

(52) U.S. Cl.
CPC ............................. *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 3,929,765 A | 12/1975 | Suzuki et al. |
| 4,576,943 A | 3/1986 | Tomcufcik et al. |
| 4,582,833 A | 4/1986 | Tomcufcik et al. |
| 5,308,852 A | 5/1994 | Girard et al. |
| 5,723,492 A | 3/1998 | Chandrakumar et al. |
| 5,952,349 A | 9/1999 | Asberom et al. |
| 6,309,561 B1 | 10/2001 | Hasegawa et al. |
| 6,372,736 B1 | 4/2002 | Kemp et al. |
| 6,380,203 B1 | 4/2002 | Bilodeau et al. |
| 6,407,140 B1 | 6/2002 | Gregory et al. |
| 6,451,798 B2 | 9/2002 | Varkhedkar et al. |
| 6,552,023 B2 | 4/2003 | Zablocki et al. |
| 6,635,644 B2 | 10/2003 | Salituro et al. |
| 6,699,873 B1 | 3/2004 | Maguire et al. |
| 6,734,184 B1 | 5/2004 | Barlaam et al. |
| 6,846,812 B2 | 1/2005 | Dalko et al. |
| 6,869,975 B2 | 3/2005 | Abe et al. |
| 6,875,483 B2 | 4/2005 | Ichihashi et al. |
| 6,924,313 B1 | 8/2005 | Sikorski et al. |
| 7,169,779 B2 | 1/2007 | Salituro et al. |
| 7,402,684 B2 | 7/2008 | Sandanayaka et al. |
| 7,645,779 B2 | 1/2010 | Abe et al. |
| 7,674,899 B2 | 3/2010 | Peters et al. |
| 7,718,669 B2 | 5/2010 | Petry et al. |
| 7,737,145 B2 | 6/2010 | Arnaiz et al. |
| 7,816,365 B2 | 10/2010 | Schiemann et al. |
| 7,820,675 B2 | 10/2010 | Johansson et al. |
| 7,820,821 B2 | 10/2010 | Mjalli et al. |
| 7,893,257 B2 | 2/2011 | Choudhury et al. |
| 7,902,181 B2 | 3/2011 | Furber et al. |
| 7,935,707 B2 | 5/2011 | Aebi et al. |
| 8,569,303 B2 | 10/2013 | Arnaiz et al. |
| 8,846,655 B2 | 9/2014 | Coats et al. |
| 9,006,235 B2* | 4/2015 | Zheng ................ C07D 487/04 514/230.5 |
| 9,315,509 B2 | 4/2016 | Arnaiz et al. |
| 2004/0006114 A1 | 1/2004 | Coleman et al. |
| 2004/0198777 A1 | 10/2004 | Ghosh et al. |
| 2005/0043378 A1 | 2/2005 | Axe et al. |
| 2005/0043379 A1 | 2/2005 | Axe et al. |
| 2005/0113408 A1 | 5/2005 | Helgadottir et al. |
| 2006/0063784 A1 | 3/2006 | Wang et al. |
| 2006/0223792 A1 | 10/2006 | Butler et al. |
| 2007/0155726 A1 | 7/2007 | Arnaiz et al. |
| 2008/0096906 A1 | 4/2008 | Galley et al. |
| 2009/0233922 A1 | 9/2009 | Zhuo |

(Continued)

FOREIGN PATENT DOCUMENTS

| | | |
|---|---|---|
| CN | 102030700 A | 4/2011 |
| CN | 103159742 A | 6/2013 |

(Continued)

OTHER PUBLICATIONS

Arnaiz, D., et al, U.S. Appl. No. 15/069,484, filed on Mar. 14, 2016.
Khim, S.-K., et al., "Discovery of novel and potent aryl diamines as leukotriene A4 hydrolase inhibitors," Bioorganic & Medicinal Chemistry Letters, 18 (2008) 3895-3898.
Connors, K. A., "The Stability of Cyclodextrin Complexes in Solution," Chem. Rev., 97: 1325-1357 (1997).
Jantzen and Robinson, "Modern Pharmaceutics," p. 596 (1996).
Vippagunta, S. R., et al., "Crystalline Solids," Advanced Drug Delivery reviews, 48: 3-26 (2001).
Mitchell, R. H., et al., "The Neutral Deoxygenation (Reduction) of Aryl Carbonyl Compounds With Raney-Nickel. An Alternative to the Clemmenson, Wolf-Kishner or Mozingo (Thioketal) Reductions." Tetrahedron Letters, 21 (1980).

(Continued)

Primary Examiner — Brian McDowell
(74) Attorney, Agent, or Firm — Elmore Patent Law Group, P.C.; Mahreen Hoda; Carolyn Elmore

(57) ABSTRACT

The present invention is directed to compounds encompassed by the Formula (I):

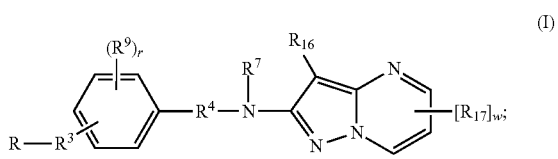

pharmaceutical compositions thereof, methods for inhibiting LTA-4 hydrolase, and methods for the treatment of a disease and disorder which is ameliorated by the inhibition of $LTA4_h$ activity. Non-limiting examples of such diseases and conditions include inflammatory and autoimmune diseases and disorders.

26 Claims, No Drawings

(56) References Cited

U.S. PATENT DOCUMENTS

| | | |
|---|---|---|
| 2010/0029619 A1 | 2/2010 | Uchikawa et al. |
| 2010/0029657 A1 | 2/2010 | Levin et al. |
| 2010/0069417 A1 | 3/2010 | Bouaboula et al. |
| 2010/0093668 A1 | 4/2010 | Babin et al. |
| 2010/0099694 A1 | 4/2010 | Babin et al. |
| 2011/0105475 A1 | 5/2011 | Roche et al. |
| 2012/0028954 A1 | 2/2012 | Goff et al. |
| 2012/0302610 A1 | 11/2012 | Chakravarty et al. |
| 2013/0123243 A1 | 5/2013 | Arnaiz et al. |
| 2016/0067226 A1 | 3/2016 | Springman et al. |
| 2016/0068522 A1 | 3/2016 | Guilford et al. |
| 2016/0068524 A1 | 3/2016 | Guilford |
| 2016/0272649 A1 | 9/2016 | Arnaiz et al. |

FOREIGN PATENT DOCUMENTS

| | | |
|---|---|---|
| EP | 1611902 A1 | 1/2006 |
| GB | 1221006 A | 2/1971 |
| JP | 2001354657 A | 12/2001 |
| JP | 2005008581 A | 1/2005 |
| WO | 02/064211 A1 | 8/2002 |
| WO | 02/069901 A2 | 9/2002 |
| WO | 02/069901 A3 | 9/2002 |
| WO | 02/072621 A2 | 9/2002 |
| WO | 02/072621 A3 | 9/2002 |
| WO | 03/010158 A1 | 2/2003 |
| WO | 03/037271 A2 | 5/2003 |
| WO | 2004/035746 A2 | 4/2004 |
| WO | 2004089410 A1 | 10/2004 |
| WO | 2004/099164 A1 | 11/2004 |
| WO | 2005/027886 A2 | 3/2005 |
| WO | 2005/027886 A3 | 3/2005 |
| WO | 2005/054246 A2 | 6/2005 |
| WO | 2007007069 A1 | 1/2007 |
| WO | 2010011912 A1 | 1/2010 |
| WO | 2011071758 A1 | 6/2011 |
| WO | 2012/067822 A1 | 5/2012 |
| WO | 2012/125832 A2 | 9/2012 |

OTHER PUBLICATIONS

Fieser, L. and Fieser, M., "Reagents for Organic Synthesis," vol. 1: 723-730 (1974) Wiley: NY.

Wolff, M. E., "Burger's Medicinal Chemistry and Drug Discovery," 5th ed., vol. 1: 975-977 (1995).

Labaudinière, R., et al., "w-[(w-Arylalkyl)aryl]alkanoic Acids: A New Class of Specific LTA4 Hydrolase Inhibitors," J. Med. Chem., 35: 3156-3169 (1992).

Penning, T. D., et al., "Structure-Activity Relationship Studies on 1-[2-(4-Phenylphenoxy)ethyl]pyrrolidine (SC-22716), a Potent Inhibitor of Leukotriene A4 (LTA4) Hydrolase," J. Med. Chem., 43: 721-735 (2000).

Beaumont, K., et al., "Design of Ester Prodrugs to Enhance Oral Absorption of Poorly Permeable Compounds: Challenges to the Discovery Scientist," Current Drug Metabolism, 4: 461-485 (2003).

Rautio, J., et al., "Prodrugs: Design and Clinical Applications," Nature Reviews, 7: 255-270 (2008).

Shen, H. C. et a;., "A strategy of employing aminoheterocycles as amide mimics to identify novel, potent and bioavailable soluble epoxide hydrolase inhibitors," Bioorganic & Medicinal Chemistry Letters, 19: 5716-5721 (2009).

Shim, Y. M. and Paige, M., "Leukotriene A4 Hydrolase—An Evolving Therapeutic Target," Inflammatory Diseases—Immunopathology, Clinical and Pharmacological Bases, Dr Mahin Khatami (Ed.), InTech, pp. 253-278 (2012).

Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.

STN—Chemical database Registry RN 1322312-60-6 for N-[(3-phenoxyphenyl)methyl]-6-(1-piperidinyl)-3-Pyridinemethanamine, Entered STN: Aug. 24, 2011.

Online: "http://web.archive.org/web/20120301075525/http://www.fchgroup.net/products.php" dated Mar. 1, 2012 accessed Oct. 12, 2016.

Hutchins, T. O., et al., "Selective Reductive Displacement of Alkyl Halides and Sulfonate Esters with Cyanoborohydride Reagents in Hexamethylphosphoramide," J. Org. Chem., 42(1): 82-91 (1977).

Online "http://web.archive.org/web/20031225052253/http://www.specs.net/", Dec. 25, 2003, accessed Apr. 1, 2015.

Online "http://web.archive.org/web/20120317091129/http://www.fchgroup.net/" dated Mar. 1, 2012, accessed Oct. 12, 2016.

Online "http://web.archive.org/web/20130122020518/http://www.chembridge.com/screening_libraries/" 2011, accessed Oct. 10, 2015.

Pitt, W. R., et al., "Heteroaromatic Rings of the Future," J. Med. Chem., 52: 2952-2963 (2009).

Pozharskii, et al., Heterocycles in Life and Society Wiley, pp. 1-6 (1997).

Banker, G.S., et al., "Modern Pharmaceutics, 3ed.," Marcel Dekker, Inc., NY, pp. 451 and 596 (1996).

Hauptmann and Walter, Chem. Rev., 62: 347-404 (1962).

Martin, Y. C., et al., "Do Structurally Similar Molecules Have Similar Biological Activity?," J. Med. Chem., 45: (2002). 4350-4358.

Arnaiz, D., et al., "Diamine derivatives as inhibitors of leukotriene A4 hydrolase and their preparation, pharmaceutical compositions and use in the treatment of inflammatory disorders," CA147: 166353 (2007).

Breitenstein, W., et al., "Preparation of substituted pyrrolidines as renin inhibitors," CA145: 103533 (2006).

Bridger, G. J., et al., "Preparation of piperidines as chemokine receptor, particularly CCR5, modulators for treatment of inflammatory and autoimmune diseases," CA143: 97274 (2005).

Brodin, P., et al., "Benzamides, pyridopyrimidines and related compounds as antiinfective compounds and their preparation and use in the treatment of tuberculosis," CA152: 168983 (2010).

Coats, S. J., et al., "4-Substituted 2-phenoxyphenylamines as delta opioid receptor modulators and their preparation and use in the treatment of diseases," CA154: 540153 (2011).

Kurimura, M., et al., "Preparation of N,N-substituted 3-aminopyrrolidine compounds useful as monoamines reuptake inhibitors," CA149: 53863 (2008).

Skerlj, R., et al., "Design and synthesis of pyridin-2-ylmethylaminopiperidin-1-ylbutyl amide CCR5 antagonists that are potent inhibitors of M-tropic (RS) HIV-1 replication," CA156: 10919 (2011).

Greene, T. W., "Protective Groups in Organic Synthesis," John Wiley & Sons: NY, p. 218-220, 224, 251 (1982).

* cited by examiner

INHIBITORS OF LEUKOTRIENE A4 HYDROLASE

RELATED APPLICATIONS

This application is a continuation of International Application No. PCT/US2014/027428, which designated the United States and was filed on Mar. 14, 2014, published in English, which claims the benefit of U.S. Provisional Application No. 61/781,193, filed on Mar. 14, 2013. The entire teachings of the above application are incorporated herein by reference.

BACKGROUND OF THE INVENTION

Leukotriene $B_4$ ($LTB_4$) is a potent pro-inflammatory activator of inflammatory cells, including neutrophils (J. Palmblad, *J. Rheumatol.* 1984, 13(2):163-172), eosinophils (A. M. Tager, et al., *J. Exp. Med.* 2000, 192(3):439-446), monocytes (N. Dugas et al., *Immunol.* 1996, 88(3):384-388), macrophages (L. Gagnon et al., *Agents Actions* 1989, 34(1-2):172-174), T cells (H. Morita et al., *Biochem. Biophys. Res. Commun.* 1999, 264(2):321-326) and B cells (B. Dugas et al., *J. Immunol.*1990, 145(10):3405-3411). Immune cell priming and activation by $LTB_4$ can promote chemotaxis, adhesion, free radical release, degranulation and cytokine release. $LTB_4$ stimulates T-cell proliferation and cytokine release in response to IL-2, concanavalin-A and CD3 ligation (H. Morita et al., *Biochem. Biophys. Res. Commun.* 1999, 264(2):321-326). $LTB_4$ is a chemoattractant for T-cells creating a functional link between early innate and late adaptive immune responses to inflammation (K. Goodarzi, et al., *Nat. Immunol.* 2003, 4:965-973; V. L. Ott, et al., *Nat. Immunol.* 2003, 4:974-981; A. M. Tager, et al., *Nat. Immunol.* 2003, 4:982-990). There is substantial evidence that $LTB_4$ plays a significant role in the amplification of many inflammatory disease states (R. A. Lewis et al., *N. Engl. J. Med.* 1990, 323:645; W. R. Henderson, *Ann. Intern. Med.* 1994, 121:684) including asthma (D. A. Munafo et al., *J. Clin. Invest.* 1994, 93(3):1042-1050), inflammatory bowel disease (IBD) (P. Sharon and W. F. Stenson, *Gastroenterology* 1984, 86(3):453-460), chronic obstructive pulmonary disease (COPD) (P. J. Barnes, *Respiration* 2001, 68(5):441-448), arthritis (R. J. Griffiths et al., *Proc. Natl. Acad. Sci. U.S.A.* 1995, 92(2):517-521; F. Tsuji et al., *Life Sci.* 1998 64(3):L51-L56), psoriasis (K. Ikai, *J. Dermatol. Sci.* 1999, 21(3):135-146; Y. I. Zhu and M. J. Stiller, *Skin Pharmacol. Appl. Skin Physiol.* 2000, 13(5):235-245), and atherosclerosis (E. B. Friedrich, et al., *Arterioscler. Thromb. Vasc. Biol.* 2003, 23:1761-1767; K. Subbarao, et al., *Arterioscler. Thromb. Vasc. Biol.* 2004, 24:369-375; A. Helgadottir, et al., *Nat. Genet.* 2004, 36:233-239; V. R. Jala, et al., *Trends in Immun.* 2004, 25:315-322). $LTB_4$ also simulates the production of various cytokines and may play a role in immunoregulation (A. W. Ford-Hutchinson, *Immunology* 1990, 10:1). Furthermore, it has been shown that $LTB_4$ levels are elevated in brochoalveolar lavage fluid from patients with scleroderma lung disease (see Kowal-Bielecka, O. et al., *Arthritis Rheum.*(Nov. 30, 2005), Vol. 52, No. 12, pp. 3783-3791). Therefore, a therapeutic agent that inhibits the biosynthesis of LTB4 or the response of cells to $LTB_4$ may be useful for the treatment of these inflammatory conditions.

The biosynthesis of $LTB_4$ from arachidonic acid (AA) involves the action of three enzymes: phospholipase $A_2$ ($PLA_2$), to release AA from the membrane lipids; 5-lipoxygenase (5-LO), to form the unstable epoxide Leukotriene $A_4$ ($LTA_4$); and leukotriene $A_4$ hydrolase ($LTA_4$-h), to form $LTB_4$ (A. W. Ford-Hutchinson, et al., *Annu. Rev. Biochem.* 1994, 63:383-347). The cysteinyl leukotrienes are formed by the addition of glutathione to $LTA_4$ by the action of $LTC_4$ synthase (Aharony, D., *Am. J. Respir. Crit. Care Med.* 1998, 157 (6, Pt 2), S214-S218) into the pro-inflammatory cysteinyl leukotrienes $LTC_4$, $LTD_4$ and $LTE_4$. An alternative path for $LTA_4$ is conversion via transcellular biosynthesis and the action of lipoxygenases into lipoxin $A_4$ ($LXA_4$) and lipoxin $B_4$ ($LXB_4$) (C. N. Serhan, *Prostaglandins* 1997, 53:107-137).

$LTA_4$-h is a monomeric, soluble 69 kD zinc metalloenzyme. A high resolution crystal structure of recombinant $LTA_4$-h with bound inhibitors has been obtained (M. M. Thunissen et al., *Nat Struct. Biol.* 2001, 8(2): 131-135). $LTA_4$-h is a bifunctional zinc-dependent metalloenzyme of the M1 class of metallohydrolases. It catalyses two reactions: the stereospecific epoxide hydrolase reaction to convert $LTA_4$ to $LTB_4$ and a peptidase cleavage of chromogenic substrates. The Zn center is critical to both activities. $LTA_4$-h is related to aminopeptidases M and B, which have no $LTA_4$-hydrolase activity. $LTA_4$-h has high substrate specificity, accepting only a 5,6-trans-epoxide with a free carboxylic acid at C-1 of the fatty acid. The double-bond geometry of the substrate is essential for catalysis. In contrast, $LTA_4$-h peptidase activity appears to be promiscuous, cleaving nitroanilide and 2-naphthylamide derivatives of various amino acids, e.g. in particular alanine and arginine. Arg-Gly-Asp, Arg-Gly-Gly, and Arg-His-Phe tripeptides are hydrolyzed with specificity constants ($k_{cat}/K_m$) similar to the epoxide hydrolase reaction. There is no known physiological peptide substrate for $LTA_4$-h.

$LTA_4$-h is widely expressed as a soluble intracellular enzyme in intestine, spleen, lung and kidney. High activity levels are found in neutrophils, monocytes, lymphocytes and erythrocytes. Tissue macrophages can have high $LTA_4$-h levels. An interesting feature is that the cellular distribution of $LTA_4$-h and 5-LO are distinct, requiring close apposition of cells such as neutrophils and epithelial cells for efficient transcellular $LTB_4$ synthesis. Many studies support this concept, including data from bone marrow chimeras derived from $LTA_4$-h$^{-/-}$ and 5-LO$^{-/-}$ mice (J. E. Fabre et al., *J. Clin. Invest.* 2002, 109(10):1373-1380).

Studies have shown that introduction of exogenous $LTB_4$ into normal tissues can induce inflammatory symptoms (R. D. R. Camp et al., *Br. J. Pharmacol.* 1983, 80(3):497-502; R. Camp et al., *J. Invest. Dermatol.* 1984, 82(2):202-204). Elevated levels of $LTB_4$ have been observed in a number of inflammatory diseases including inflammatory bowel disease (IBD), chronic obstructed pulmonary disease (COPD), psoriasis, rheumatoid arthritis (RA), cystic fibrosis, multiple sclerosis (MS), and asthma (S. W. Crooks and R. S. Stockley, *Int. J. Biochem. Cell Biol.* 1998, 30(2):173-178). Therefore, reduction of $LTB_4$ production by an inhibitor of $LTA_4$-h activity would be predicted to have therapeutic potential in a wide range of diseases. This idea is supported by a study of $LTA_4$-h-deficient mice that, while otherwise healthy, exhibited markedly decreased neutrophil influx in arachidonic acid-induced ear inflammation and zymosan-induced peritonitis models (R. S. Byrum et al., *J. Immunol.* 1999, 163(12):6810-68129). $LTA_4$-h inhibitors have been shown to be effective anti-inflammatory agents in preclinical studies. For example, oral administration of $LTA_4$-h inhibitor SC57461 caused inhibition of ionophore-induced LTB4 production in mouse blood ex vivo, and in rat peritoneum in vivo (J. K. Kachur et al., *J. Pharm,. Exp. Thr.* 2002, 300(2): 583-587). Eight weeks of treatment with the same inhibitor significantly improved colitis symptoms in cotton top tamarins (T. D. Penning, *Curr. Pharm. Des.* 2001, 7(3):163-179). The spontaneous colitis that develops in these animals is very similar to human IBD. The results therefore indicate that $LTA_4$-h inhibitors would have therapeutic utility in this and other human inflammatory diseases.

Events that elicit the inflammatory response include the formation of the pro-inflammatory mediator $LTB_4$, which can be blocked with an $LTA_4$-h inhibitor, thus providing the ability to prevent and/or treat leukotriene-mediated conditions, such as inflammation. $LTA_4$-h inhibitors have been described, for example, in U.S. Pat. No. 7,737,145 and U.S. Patent Application Publication No. 20100210630A1, the contents of each of which are incorporated by reference herein.

It would be advantageous to develop additional $LTA_4$-h inhibitors.

SUMMARY OF THE INVENTION

The present invention is directed to compounds encompassed by the Formula (I), pharmaceutical compositions thereof, methods for inhibiting $LTA_4$ hydrolase, and methods for the treatment of a disease and disorder which is ameliorated by the inhibition of $LTA_4$-h activity. Non-limiting examples of such diseases and conditions include inflammatory diseases and disorder, autoimmune diseases and disorders and cancer.

In one embodiment, the invention is directed to a compound having the Formula (I):

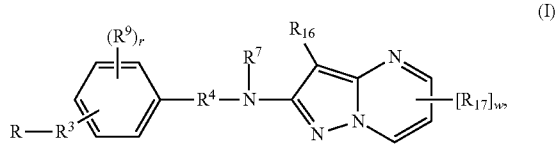

wherein:
R is i) the group;

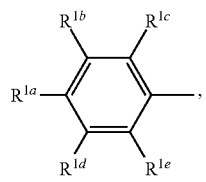

or
ii) the group;

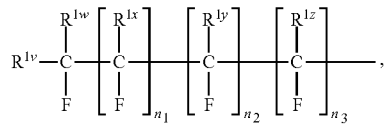

or
iii) an optionally substituted heteroaryl;
$n_1$, $n_2$, and $n_3$ are each independently 0 to 2;
r is 0 to 4;
$R^{1a}$, $R^{1b}$, $R^{1c}$, $R^{1d}$ and $R^{1e}$ are each independently hydrogen, $OR^{10}$, $C(O)OR^{10}$, $C(O)R^{10}$, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, or optionally substituted heterocyclyl;

$R^{1v}$, $R^{1w}$, $R^{1x}$, $R^{1y}$ and $R^{1z}$ are each independently hydrogen or fluoro;

$R^3$ is a direct bond, —O—, —$R^{12}$—O—, —O—$R^{12}$—, —O—$R^{12}$—O—, an optionally substituted straight or branched $C_1$ to $C_{12}$ alkylene chain, an optionally substituted straight or branched $C_2$ to $C_{12}$ alkenylene chain, or an optionally substituted straight or branched $C_3$ to $C_{12}$ alkynylene chain;

$R^4$ is a direct bond, —O—$R^{12a}$, an optionally substituted straight or branched $C_1$ to $C_{12}$ alkylene chain, an optionally substituted straight or branched $C_2$ to $C_{12}$ alkenylene chain, or an optionally substituted straight or branched $C_3$ to $C_{12}$ alkynylene chain;

$R^7$ is hydrogen, $OR^{10}$, $C(O)R^{10}$, $C(O)OR^{10}$, $C(O)$—$R^{13}$—$N(R^{10})R^{11}$, $N(R^{10})C(O)N(R^{10})R^{11}$, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, optionally substituted aryl, optionally substituted heteroaryl, and optionally substituted heterocyclyl;

each $R^9$ is independently —$OR^{10}$, optionally substituted $C_1$-$C_{12}$ alkyl, optionally substituted $C_2$-$C_{12}$ alkenyl, optionally substituted $C_2$-$C_{12}$ alkynyl, halo, aryl, or heteroaryl;

each $R^{10}$ and $R^{11}$ is independently hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, optionally substituted aryl, optionally substituted heteroaryl, and optionally substituted heterocyclyl;

or $R^{10}$ and $R^{11}$, together with the nitrogen to which they are attached, form an optionally substituted N-heterocyclyl or an optionally substituted N-heteroaryl;

$R^{12}$ is an optionally substituted straight or branched $C_1$ to $C_{12}$ alkylene chain, an optionally substituted straight or branched $C_2$ to $C_{12}$ alkenylene chain, or an optionally substituted straight or branched $C_3$ to $C_{12}$ alkynylene chain;

$R^{12a}$ is an optionally substituted straight or branched $C_1$ to $C_{12}$ alkylene chain, an optionally substituted straight or branched $C_2$ to $C_{12}$ alkenylene chain, or an optionally substituted straight or branched $C_3$ to $C_{12}$ alkynylene chain;

each $R^{13}$ is independently a direct bond, an optionally substituted straight or branched $C_1$ to $C_{12}$ alkylene chain, an optionally substituted straight or branched $C_2$ to $C_{12}$ alkenylene chain, or an optionally substituted straight or branched $C_3$ to $C_{12}$ alkynylene chain; and $R^{16}$ is selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, optionally substituted heterocyclyl, $OR^{10}$, $C(O)R^{10}$, $C(O)OR^{10}$, $C(O)$—$R^{13}$—$N(R^{10})R^{11}$, $N(R^{10})C(O)N(R^{10})R^{11}$, $NR_{10}R_{11}$, and $N(R_{10})C(O)R_{10}$;

Each $R^{17}$ is independently selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, optionally substituted heterocyclyl, $OR^{10}$, $NO_2$, $S(O)_jR^{10}$, S(O)jNR$^{10}$R$^{11}$, C(O)R$^{10}$, C(O)OR$^{10}$, C(O)—R$^{13}$—N(R$^{10}$)R$^{11}$, N(R$^{10}$)C(O)N(R$^{10}$)R$^{11}$, NR$_{10}$R$_{11}$, and N(R$_{10}$)C(O)R$_{10}$;

wherein w is an integer from 1 to 3; and j is 0, 1, or 2;

as a single stereoisomer or as a mixture of stereoisomers; or a pharmaceutically acceptable salt, solvate, polymorph, clathrate, ammonium ion, N-oxide or prodrug thereof.

The invention is also directed to a pharmaceutical composition comprising a pharmaceutically acceptable excipient and a compound of Formula (I), as a single stereoisomer or as a mixture of stereoisomers; or a pharmaceutically acceptable salt, solvate, polymorph, clathrate, ammonium ion, N-oxide or prodrug thereof.

Also encompassed, is a method of treating a disease or disorder ameliorated by the inhibition of leukotriene A$_4$ (LTA$_4$) hydrolase activity in a mammal, wherein the method comprises administering to a mammal in need thereof a therapeutically effective amount of a compound of Formula (I), as a single stereoisomer or as a mixture of stereoisomers; or a pharmaceutically acceptable salt, solvate, polymorph, clathrate, ammonium ion, N-oxide or prodrug thereof. In some aspects, the disease or disorder is an inflammatory disorder or autoimmune disorder.

DETAILED DESCRIPTION OF THE INVENTION

A description of preferred embodiments of the invention follows.

As used herein, the words "a" and "an" are meant to include one or more unless otherwise specified. For example, the term "a cell" encompasses both a single cell and a combination of two or more cells.

As discussed above, the present invention is directed to compounds of Formula (I), as a single stereoisomer or as a mixture of stereoisomers; or a pharmaceutically acceptable salt, solvate, polymorph, clathrate, ammonium ion, N-oxide or prodrug thereof, pharmaceutical compositions of any of thereof, and methods comprising administering a compound of the invention to a subject for the treatment of disorders and diseases that can be ameliorated by inhibition of LTA4-h.

In some embodiments, the invention is directed to a compound of Formula (I), as a single stereoisomer or as a mixture of stereoisomers; or a pharmaceutically acceptable salt, solvate, polymorph, clathrate, ammonium ion, N-oxide or prodrug thereof, wherein R$_{16}$ is selected from the group consisting of cyano, OR$^{10}$, C(O)R$^{10}$, C(O)OR$^{10}$, and C(O)—R$^{13}$—N(R$^{10}$)R$^{11}$. In some embodiments, R$^{16}$ is cyano.

In additional embodiments, the invention is a compound of Formula (I), as a single stereoisomer or as a mixture of stereoisomers; or a pharmaceutically acceptable salt, solvate, polymorph, clathrate, ammonium ion, N-oxide or prodrug thereof, wherein w is 1 and R$_{17}$ is selected from the group consisting of optionally substituted aryl, optionally substituted heteroaryl and C(O)R$_{20}$, wherein R$_{20}$ is optionally substituted aryl and optionally substituted heteroaryl.

In yet additional aspects, the compound has the Formula (Ia):

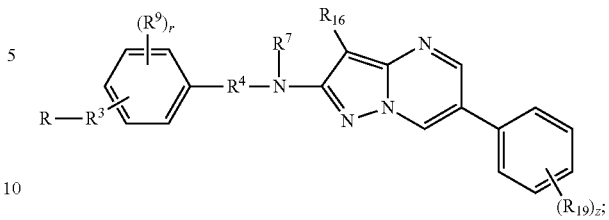

(Ia)

as a single stereoisomer or as a mixture of stereoisomers; or a pharmaceutically acceptable salt, solvate, polymorph, clathrate, ammonium ion, N-oxide or prodrug thereof, wherein each R$_{19}$ is independently selected from the group consisting of hydrogen, optionally substituted C$_1$-C$_{12}$ alkyl, optionally substituted C$_2$-C$_{12}$ alkenyl, optionally substituted C$_2$-C$_{12}$ alkynyl, optionally substituted C$_3$-C$_{15}$ cycloalkyl, optionally substituted C$_3$-C$_{15}$ cycloalkenyl, halo, cyano, optionally substituted aryl, optionally substituted heteroaryl, optionally substituted heterocyclyl, OR$^{10}$, NO$_2$, S(O)$_j$R$^{10}$, S(O)$_j$NR$^{10}$R$^{11}$, C(O)R$^{10}$, C(O)OR$^{10}$, C(O)—R$^{13}$—N(R$^{10}$)R$^{11}$, N(R$^{10}$)C(O)N(R$^{10}$)R$^{11}$, NR$_{10}$R$_{11}$, and N(R$_{10}$)C(O)R$_{10}$; and wherein z is an integer from 1 to 5. In some embodiments, R$^{19}$ is independently selected from the group consisting of hydrogen, hydroxyl, halo, optionally substituted C$_1$-C$_4$ alkyl, C(O)R$^{10}$, C(O)OR$^{10}$, NO$_2$, S(O)$_j$R$^{10}$ and S(O)$_j$NR$^{10}$R$^{11}$. In certain aspects, R$_{16}$ is cyano.

In yet additional aspects of the invention, the compound has the Formula (Ib):

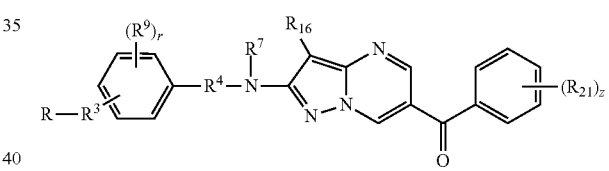

as a single stereoisomer or as a mixture of stereoisomers; or a pharmaceutically acceptable salt, solvate, polymorph, clathrate, ammonium ion, N-oxide or prodrug thereof, wherein each R$_{21}$ is independently selected from the group consisting of hydrogen, optionally substituted C$_1$-C$_{12}$ alkyl, optionally substituted C$_2$-C$_{12}$ alkenyl, optionally substituted C$_2$-C$_{12}$ alkynyl, optionally substituted C$_3$-C$_{15}$ cycloalkyl, optionally substituted C$_3$-C$_{15}$cycloalkenyl, halo, cyano, optionally substituted aryl, optionally substituted heteroaryl, optionally substituted heterocyclyl, OR$^{10}$, NO$_2$, S(O)$_j$R$^{10}$, S(O)$_j$NR$^{10}$R$^{11}$; C(O)R$^{10}$, C(O)OR$^{10}$, C(O)—R$^{13}$—N(R$^{10}$)R$^{11}$, N(R$^{10}$)C(O)N(R$^{10}$)R$^{11}$, NR$_{10}$R$_{11}$, and N(R$_{10}$)C(O)R$_{10}$; and wherein z is an integer from 1 to 5. In some aspects, each R$^{21}$ is independently selected from the group consisting of hydrogen, hydroxyl, halo, optionally substituted C$_1$-C$_4$ alkyl, C(O)R$^{10}$, C(O)OR$^{10}$, NO$_2$, S(O)$_j$R$^{10}$ and S(O)$_j$NR$^{10}$R$^{11}$. In yet additional aspects of the invention, each R$^{21}$ is independently selected from the group consisting of hydrogen, hydroxyl and halo.

In yet other embodiments, the compound has the Formula (I), as a single stereoisomer or as a mixture of stereoisomers; or a pharmaceutically acceptable salt, solvate, polymorph, clathrate, ammonium ion, N-oxide or prodrug thereof, wherein R$^{17}$ is optionally substituted heteroaryl. In some aspects of the invention, R$^{17}$ is an optionally substituted heteroaryl containing one or more ring nitrogen atoms. In yet additional embodiments, $R^{17}$ is and optionally substituted pyridyl.

In some embodiments, the invention is a compound described herein, as a single stereoisomer or as a mixture of stereoisomers; or a pharmaceutically acceptable salt, solvate, polymorph, clathrate, ammonium ion, N-oxide or prodrug thereof, wherein R is the group:

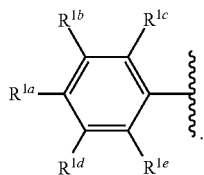

In certain embodiments, $R^{1a}$ is hydrogen, $C(O)OR^{10}$, $C(O)R^{10}$, $C(O)NR^{10}R^{11}$, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$cycloalkyl, optionally substituted $C_3$-$C_{15}$cycloalkenyl, halo, cyano, optionally substituted aryl, optionally substituted heteroaryl, and optionally substituted heterocyclyl. In additional aspects, $R^{1a}$ is hydrogen, $C(O)OR^{10}$, $C(O)R^{10}$, $C(O)NR^{10}R^{11}$, optionally substituted alkyl, halo, optionally substituted phenyl, furanyl, thienyl, thiazolyl, or optionally substituted oxazolyl; and wherein $R^{1b}$, $R^{1c}$, , $R^{1d}$ and $R^{1e}$ are each hydrogen. In yet additional embodiments, $R^{1a}$ is halo. In additional aspects, $R^{1a}$ is oxazolyl or thiazolyl.

In additional embodiments, the invention is a compound described herein, as a single stereoisomer or as a mixture of stereoisomers; or a pharmaceutically acceptable salt, solvate, polymorph, clathrate, ammonium ion, N-oxide or prodrug thereof, wherein, R is the group:

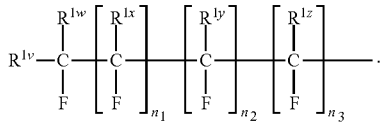

In yet another aspect, the invention is a compound described herein, as a single stereoisomer or as a mixture of stereoisomers; or a pharmaceutically acceptable salt, solvate, polymorph, clathrate, ammonium ion, N-oxide or prodrug thereof, wherein R is an optionally substituted heteroaryl. In certain aspects, R is furanyl, oxazolyl, pyrazolyl, pyridinyl, triazolyl, thiazolyl, or benzothiazolyl, each of which is optionally substituted. In some embodiments, R is an optionally substituted heteroaryl. In yet additional embodiments, R is furanyl, oxazolyl, pyrazolyl, pyridinyl, triazolyl, thiazolyl, or benzothiazolyl, each of which is optionally substituted.

In certain aspects, the invention is a compound described herein, as a single stereoisomer or as a mixture of stereoisomers; or a pharmaceutically acceptable salt, solvate, polymorph, clathrate, ammonium ion, N-oxide or prodrug thereof, wherein $R^3$ is O.

In some embodiments, the invention is a compound described herein, as a single stereoisomer or as a mixture of stereoisomers; or a pharmaceutically acceptable salt, solvate, polymorph, clathrate, ammonium ion, N-oxide or prodrug thereof, wherein $R^4$ is a direct bond, an optionally substituted methylene or an optionally substituted ethylene. In certain embodiments, $R^4$ is methylene.

In certain embodiments, the invention is a compound described herein, as a single stereoisomer or as a mixture of stereoisomers; or a pharmaceutically acceptable salt, solvate, polymorph, clathrate, ammonium ion, N-oxide or prodrug thereof, wherein $R^7$ is hydrogen or optionally substituted $C_1$-$C_6$ alkyl. In additional aspects, $R^7$ is hydrogen or alkyl optionally substituted with $OR^{10}$, or alkyl optionally substituted with $NR^{10}R^{11}$. In yet another embodiment, $R^7$ is hydrogen or methyl.

Non-limiting examples of compounds encompassed by the invention are shown in Table 1 below:

TABLE 1

| Compound No. | X | Y |
|---|---|---|
| 1 | PhO | NH$_2$ |
| 2 | PhO | 4-NO$_2$, 3-SO$_2$Me-phenyl |
| 3 | PhO | 4-NO$_2$, 3-CO$_2$H-phenyl (O$_2$N position) |
| 4 | PhO | 3-NO$_2$, 2-OH-benzoyl |
| 5 | PhO | 2-OH-benzoyl |
| 6 | PhO | 3,5-diCl, 4-OH-benzoyl |

TABLE 1-continued

[Structure: 4-X-phenyl-HN attached to pyrazolo[1,5-a]pyrimidine core with CN group and Y substituent]

| Compound No. | X | Y |
|---|---|---|
| 7 | PhO | 5-chloro-2-hydroxybenzoyl |
| 8 | PhO | 2-hydroxybenzoyl |
| 9 | PhO | 2-nitro-3-carboxyphenyl |
| 10 | PhO | 3-nitro-4-carboxyphenyl |
| 11 | PhO | 6-carboxypyridin-2-yl |
| 12 | PhO | 5-carboxypyridin-2-yl |
| 13 | PhO | 2-methoxybenzoyl |

In Table 1 above, it will be understood that "Ph" is an abbreviation for phenyl.

It is to be understood that the specific embodiments described herein can be taken in combination with other specific embodiments delineated herein. It will be appreciated that the description of the present invention herein should be construed in congruity with the laws and principals of chemical bonding.

"Alkyl" refers to a straight or branched hydrocarbon chain radical consisting solely of carbon and hydrogen atoms, containing no unsaturation and which is attached to the rest of the molecule by a single bond. In some embodiments, an alkyl group has from one to twelve carbon atoms, one to eight carbon atoms, or one to six carbon atoms. Non-limiting examples of alkyl groups include methyl, ethyl, n-propyl, 1-methylethyl (iso-propyl), n-butyl, n-pentyl, 1,1-dimethylethyl (t-butyl), 3-methylhexyl, 2-methylhexyl, and the like. An optionally substituted alkyl group can by an alkyl group substituted with one or more substituents described in detail below. Non-limiting examples of optionally substituted alkyls include haloalkyl, alkyl substituted with cyano, optionally substituted aralkyl, optionally substituted heteroarylalkyl, optionally substituted cycoalklylalkyl, optionally substituted heterocycloalkyl, alkyl substituted with an amino group, alkyls substituted with hydroxyl or alkoxy, and the like.

"Alkenyl" refers to a straight or branched hydrocarbon chain radical group consisting solely of carbon and hydrogen atoms, containing at least one double bond. In some cases, an alkenyl can have from two to twelve carbon atoms, or two to eight carbon atoms. An alkenyl is attached to the rest of the molecule by a single bond, for example, ethenyl, prop-1-enyl, but-1-enyl, pent-l-enyl, penta-1,4-dienyl, and the like. An optionally substituted alkenyl group can by an alkyl group substituted with one or more substituents described in detail below.

"Alkynyl" refers to a straight or branched hydrocarbon chain radical group consisting solely of carbon and hydrogen atoms, containing at least one triple bond, optionally containing at least one double bond. In some embodiments, an alkynyl can have from two to twelve carbon atoms, or two to eight carbon atoms. An alkynyl is attached to the rest of the molecule by a single bond, for example, ethynyl, propynyl, butynyl, pentynyl, hexynyl, and the like. An optionally substituted alkynyl group can by an alkyl group substituted with one or more substituents described in detail below.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. An alkylene chain can be substituted or unsubstituted.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain.

"Alkoxy" refers to a radical of the formula —OR$_a$ where R$_a$ is an optionally substituted alkyl radical as defined above containing one to twelve carbon atoms.

"Alkoxyalkyl" refers to a radical of the formula —R$_a$—O—R$_a$ where each R$_a$ is independently an optionally substituted alkyl radical as defined above. The oxygen atom may be bonded to any carbon in either alkyl radical.

"Aryl" refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to, groups such as fluorenyl, phenyl and naphthyl.

"Aralkyl" refers to a radical of the formula —R$_a$—R$_b$ where R$_a$ is an optionally substituted alkyl radical and R$_b$ is one or more optionally substituted aryl radicals, for example, benzyl, diphenylmethyl and the like. "Aralkenyl" refers to a radical of the formula —R$_c$—R$_b$ where R$_c$ is an optionally substituted alkenyl radical and R$_b$ is one or more optionally substituted aryl radicals. "Aralkynyl" refers to a radical of the formula —R$_d$—R$_b$ where R$_d$ is an optionally substituted alkynyl radical and R$_b$ is one or more optionally substituted aryl radicals.

"Aryloxy" refers to a radical of the formula —OR$_b$ where R$_b$ is an optionally substituted aryl group. "Aralkyloxy" refers to a radical of the formula —OR$_b$ where R$_b$ is an aralkyl group. The aralkyl part of the aralkyloxy radical may be optionally substituted.

"Ammonium ion" refers to a nitrogen within a compound of the invention containing a positive charge due to the additional substitution of the nitrogen with an optionally substituted alkyl group as defined above.

"Amino" refers to the —NH$_2$ radical.
"Cyano" refers to the —CN radical.
"Hydroxy" refers to the —OH radical.
"Nitro" refers to the —NO$_2$ radical.
"Oxo" refers to the C(O) radical.

"Clathrates" as used herein refers to substances which fix gases, liquids or compounds as inclusion complexes so that the complex may be handled in solid form and the included constituent (or "guest" molecule) is subsequently released by the action of a solvent or by melting. The term "clathrate" is used interchangeably herein with the phrase "inclusion molecule" or with the phrase "inclusion complex". Clathrates used in the instant invention are prepared from cyclodextrins. Cyclodextrins are widely known as having the ability to form clathrates (i.e., inclusion compounds) with a variety of molecules. See, for example, Inclusion Compounds, edited by J. L. Atwood, J. E. D. Davies, and D. D. MacNicol, London, Orlando, Academic Press, 1984; Goldberg, I., "The Significance of Molecular Type, Shape and Complementarity in Clathrate Inclusion", Topics in Current Chemistry (1988), Vol. 149, pp. 2-44; Weber, E. et al., "Functional Group Assisted Clathrate Formation—Scissor-Like and Roof-Shaped Host Molecules", Topics in Current Chemistry (1988), Vol. 149, pp. 45-135; and MacNicol, D. D. et al., "Clathrates and Molecular Inclusion Phenomena", Chemical Society Reviews (1978), Vol. 7, No. 1, pp. 65-87. Conversion into cyclodextrin clathrates is known to increase the stability and solubility of certain compounds, thereby facilitating their use as pharmaceutical agents. See, for example, Saenger, W., "Cyclodextrin Inclusion Compounds in Research and Industry", Angew. Chem. Int. Ed. Engl. (1980), Vol. 19, pp. 344-362; U.S. Pat. No. 4,886,788 (Schering AG); U.S. Pat. No. 6,355,627 (Takasago); U.S. Pat. No. 6,288,119 (Ono Pharmaceuticals); U.S. Pat. No. 6,110,969 (Ono Pharmaceuticals); U.S. Pat. No. 6,235,780 (Ono Pharmaceuticals); U.S. Pat. No. 6,262,293 (Ono Pharmaceuticals); U.S. Pat. No. 6,225,347 (Ono Pharmaceuticals); and U.S. Pat. No. 4,935,446 (Ono Pharmaceuticals).

"Cyclodextrin" refers to cyclic oligosaccharides consisting of at least six glucopyranose units which are joined together by alpha (1-4) linkages. The oligosaccharide ring forms a torus with the primary hydroxyl groups of the glucose residues lying on the narrow end of the torus. The secondary glucopyranose hydroxyl groups are located on the wider end. Cyclodextrins have been shown to form inclusion complexes with hydrophobic molecules in aqueous solutions by binding the molecules into their cavities. The formation of such complexes protects the "guest" molecule from loss of evaporation, from attack by oxygen, visible and ultraviolet light and from intra- and intermolecular reactions. Such complexes also serve to "fix" a volatile material until the complex encounters a warm moist environment, at which point the complex will dissolve and dissociate into the guest molecule and the cyclodextrin. For purposes of this invention, the six-glucose unit containing cyclodextrin is specified as α-cyclodextrin, while the cyclodextrins with seven and eight glucose residues are designated as β-cyclodextrin and γ-cyclodextrin, respectively. The most common alternative to the cyclodextrin nomenclature is the naming of these compounds as cycloamyloses.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, and which is saturated or unsaturated and attached to the rest of the molecule by a single bond. In some aspects, a cycloalkyl will have from three to ten carbon atoms. Monocyclic radicals include, for example, cyclopropyl, cyclobutyl, cyclopentyl, cyclohexyl, cycloheptyl, and cyclooctyl. Polycyclic radicals include, for example, adamantine, norbornane, 7,7-dimethyl-bicyclo[2.2.1]heptanyl, and the like.

"Cycloalkenyl" refers to monocyclic or polycyclic hydrocarbon alkenyl moiety having 3 to fifteen carbon atoms.

The term "cycloalkynyl," refers to a monocyclic or polycyclic alkynyl moiety having 5 to 15 more carbon atoms.

"Cycloalkylalkyl" refers to a radical of the formula —R$_a$—R$_e$ where R$_a$ is an optionally substituted alkyl radical as defined above and R$_e$ is an optionally substituted cycloalkyl radical as defined above. "Cycloalkylalkenyl" refers to a radical of the formula —R$_c$—R$_e$ where R$_c$ is an optionally substituted alkenyl radical as defined above and R$_e$ is an optionally substituted cycloalkyl radical as defined above. "Cycloalkylalkynyl" refers to a radical of the formula —R$_d$-R$_e$ where R$_d$ is an optionally substituted alkynyl radical as defined above and R$_e$ is an optionally substituted cycloalkyl radical as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted.

"Haloalkenyl" refers to an alkenyl radical, as defined above, that is substituted by one or more halo radicals, as defined above. The alkenyl part of the haloalkyl radical may be optionally substituted. "Haloalkynyl" refers to an alkynyl radical, as defined above, that is substituted by one or more halo radicals, as defined above. The alkynyl part of the haloalkyl radical may be optionally substituted.

"Heterocyclyl" and "heterocyclic" refer to a stable 3- to 18-membered non-aromatic ring radical which includes one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azepinyl, 2,5-diazabicyclo[2.2.1]heptan-2-yl, hexahydro-1H-1,4-diazepinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxiranyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted.

"Heterocyclylalkyl," refers to a radical of the formula $-R_a-R_f$ where $R_a$ is an optionally substituted alkyl radical as defined above and $R_f$ is an optionally substituted heterocyclyl radical as defined above, and if the heterocyclyl is a nitrogen-containing heterocyclyl, the heterocyclyl can be attached to the alkyl radical at the nitrogen atom or a carbon atom. "Heterocyclylalkenyl" refers to a radical of the formula $-R_e-R_f$ where $R_e$ is an optionally substituted alkenyl radical as defined above and $R_f$ is an optionally substituted heterocyclyl radical as defined above, and if the heterocyclyl is a nitrogen-containing heterocyclyl, the heterocyclyl may be attached to the alkenyl radical at the nitrogen atom or at the carbon atom. "Heterocyclylalkynyl" refers to a radical of the formula $-R_d-R_f$ where $R_d$ is an optionally substituted alkynyl radical as defined above and $R_f$ is an optionally substituted heterocyclyl radical as defined above, and if the heterocyclyl is a nitrogen-containing heterocyclyl, the heterocyclyl can be attached to the alkynyl radical at the nitrogen atom or at a carbon atom.

"Heteroaryl" refers to a 3- to 18-membered fully or partially aromatic ring radical which consists of one to thirteen carbon atoms and from one to six heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; the nitrogen, carbon or sulfur atoms in the heteroaryl radical may be optionally oxidized; and the nitrogen atom may be optionally quaternized. Examples include, but are not limited to, acridinyl, benzimidazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrazolyl, pyridinyl, pyrazinyl, pyrimidinyl, pyridazinyl, pyrrolyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e. thienyl).

"N-heteroaryl" refers to an optionally substituted heteroaryl radical as defined above containing at least one nitrogen and where the point of attachment of the heteroaryl radical to the rest of the molecule is through a nitrogen atom in the heteroaryl radical.

"Heteroarylalkyl" refers to a radical of the formula $-R_a-R_g$ where $R_a$ is an optionally substituted alkyl radical as defined above and $R_g$ is an optionally substituted heteroaryl radical as defined above. "Heteroarylalkenyl" refers to a radical of the formula $-R_c-R_g$ where $R_c$ is an optionally substituted alkenyl radical as defined above and $R_g$ is an optionally substituted heteroaryl radical as defined above. "Heteroarylalkynyl" refers to a radical of the formula $-R_d-R_g$ where $R_d$ is an optionally substituted alkynyl radical as defined above and $R_g$ is an optionally substituted heteroaryl radical as defined above.

The term "substituted" refers to substitution by independent replacement of one, two, or three or more of the hydrogen atoms with substituents including, but not limited to, $-C_1-C_{12}$ alkyl, $-C_2-C_{12}$ alkenyl, $-C_2-C_{12}$ alkynyl, $-C_3-C_{15}$ cycloalkyl, $-C_3-C_{15}$ cycloalkenyl, $C_3-C_{15}$ cycloalkynyl, -heterocyclic, $-F$, $-Cl$, $-Br$, $-I$, $-OH$, $-NO_2$, $-N_3$, $-CN$, $-NH_2$, oxo, thioxo, $-NHR_x$, $-NR_xR_x$, dialkylamino, -diarylamino, -diheteroarylamino, $-OR_x$, $-C(O)OR_y$, $-C(O)R_y$, $-C(O)C(O)R_y$, $-OCO_2R_y$, $-OC(O)R_y$, $OC(O)C(O)R_y$, $-NHC(O)R_y$, $-NHCO_2R_y$, $-NHC(O)C(O)R_y$, $-NHC(S)NH_2$, $-NHC(S)NHR_x$, $-NHC(NH)NH_2$, $-NHC(NH)NHR_x$, $-NHC(NH)R_x$, $-C(NH)NHR_x$, $-NR_xC(O)R_x$, $-NR_xCO_2R_y$, $-NR_xC(O)C(O)R_y$, $-NR_xC(S)NH_2$, $-NR_xC(O)NR_xR_x$, $-NR_xS(O)_2NR_xR_x$, $-NR_xC(S)NHR_x$, $-NR_xC(NH)NH_2$, $-NR_xC(NH)NHR_x$, $-NR_xC(NH)R_x$, $-C(NR_x)NHR_x$, $-S(O)_nR_y$, $-NHSO_2R_x$, $-CH_2NH_2$, $-CH_2SO_2CH_3$, $-(C=NR_x)R_x$; -aryl, -arylalkyl, -heteroaryl, -heteroarylalkyl, -heterocycloalkyl, $-C_3-C_{15}$-cycloalkyl, -polyalkoxyalkyl, -polyalkoxy, -methoxymethoxy, -methoxyethoxy, $-SH$, $-S-R_x$, or -methylthiomethyl, wherein $R_x$ is selected from the group consisting of hydrogen, $-C_1-C_{12}$ alkyl, $-C_2-C_{12}$ alkenyl, $-C_2-C_{12}$ alkynyl, $-C_3-C_{15}$ cycloalkyl, -aryl, -heteroaryl and -heterocyclic; $-R_y$ is selected from the group consisting of hydrogen, $-C_1-C_{12}$ alkyl, $-C_2-C_{12}$ alkenyl, $-C_2-C_{12}$ alkynyl, $-C_3-C_{15}$ cycloalkyl, -aryl, -heteroaryl, -heterocyclic, $-NH_2$, $-NH-C_1-C_{12}$ alkyl, $-NH-C_2-C_{12}$ alkenyl, $-NH-C_2-C_{12}$-alkynyl, $-NH-C_3-C_{15}$ cycloalkyl, $-NH$-aryl, $-NH$-heteroaryl and $-NH$-heterocyclic, and n is 0, 1 or 2. It is understood that the aryls, heteroaryls, alkyls, cycloalkyls, heterocyclics and the like can be further substituted.

"Polymorph" refers to a polymorphic form of compound of the invention. Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. In this case, the metastable form, although less stable, may exhibit properties desirable over those of the stable form, such as enhanced solubility or better oral bioavailability.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. In some embodiments, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which, for example, has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients.

"Solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

"Therapeutically effective amount" refers to that amount of a compound of the invention that, when administered to a mammal, preferably a human, is sufficient to effect treatment, as defined below, of a disease or condition of interest in the mammal, preferably a human. The amount of a compound of the invention which constitutes a "therapeutically effective amount" will vary depending on, for example, the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy, but it can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes, for example: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; and/ or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, such as for example, but not limited to, HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposeable mirror images of one another.

A "tautomer" refers to a proton shift from one atom of a molecule to another atom of the same molecule. The present invention includes tautomers of any said compounds.

Compounds of the invention can be prepared using methods that have been described in the literature, for example, in U.S. Pat. No. 7,737,145 and U.S. Patent Application Publication No. 20100210630A1, the contents of each of which are expressly incorporated by reference herein. Relevant methods are also described, for example, in Baraldi et al. (2003), *J Med Chem* 46:1229-1241, the contents of which are expressly incorporated by reference herein. As will be understood by the skilled artisan, diastereomers can be separated from the reaction mixture using column chromatography.

Methods for the preparation of compounds of the invention are also illustrated in the Examples section below.

It will be appreciated by those skilled in the art that in the methods described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)R" (wherein R" is alkyl, aryl or arylalkyl), p-methoxybenzyl, trityl and the like. Suitable protecting groups for carboxylic acid include alkyl, aryl or arylalkyl esters.

Protecting groups can be added or removed in accordance with standard techniques, which are known to one skilled in the art and as described herein. The use of protecting groups is described in detail in Greene, T. W. and P. G. M. Wuts, Protective Groups in Organic Synthesis (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is understood that one of ordinary skill in the art would be able to make the compounds of the invention by methods similar to the methods described herein or by methods known to one of ordinary skill in the art. In general, compounds employed as initial starting materials in the synthesis of the compounds of the invention are well known and commercially available. To the extent that the compounds employed as initial starting materials are not commercially available, the compounds may be readily synthesized using specific references provided, or by standard procedures commonly employed by those of ordinary skill in the art and/or found in general references text (see, for example, Comprehensive Organic Transformations, VCH Publishers Inc., 1989; Compendium of Organic Synthetic Methods, Volumes 1-10, 1974-2002, Wiley Interscience; Advanced Organic Chemistry: Reactions, Mechanisms, and Structure, 5th edition, Wiley Interscience, 2001; Advanced Organic Chemistry, 4th Edition, Part B, Reactions and Synthesis, Kluwer Academic/Plenum Publishers, 2000, etc., and references cited therein).

The following common abbreviations are used:
DMF for N,N-dimethylformamide
THF for tetrahydrofuran
TFA for trifluoroacetic acid
EtOAc for ethyl acetate
TMS for trimethylsilyl
TLC for thin layer chromatography
MeOH for methanol
NaOH for sodium hydroxide
Boc for t-butoxycarbonyl.

The compounds of the invention can be tested for their ability to inhibit $LTA_4$-h by various known assays and by assays described herein. For example, the compounds can be tested for their ability to inhibit $LTA_4$-h activity by assaying the compounds in the hydrolase-homogeneous time resolved fluoroescence assay. This assay, which is a two-step assay, measures the hydrolysis of $LTA_4$-h to $LTB_4$ by analyzing the amount of $LTB_4$ produced. The first step involves the enzymatic conversion of $LTA_4$-h to $LTB_4$ and the second step involves the quantification of the $LTA_4$-h formed with a homogeneous time resolved fluoroescence assay.

Since $LTA_4$-h hydrolase is grouped with the M1 family of zinc metalloproteases (see, Rudberg, P. C. et al., J. Biol. Chem. 2002, Vol. 277, page 1398-1404), the compounds of the invention can be tested in the standard hydrolase and peptidase assay to determine the compounds' kinetic constants for binding to $LTA_4$-h hydrolase and for inhibiting $LTB_4$ synthesis (see Askonas, L. J., et al., The Journal of Pharmacology and Experimental Therapeutics 2002, 300(2): 577-582; Penning, T. D., J. Med. Chem. 2000, 43(4): 721-735; Kull, F. et al., The Journal of Biological Chemistry 1999, 274 (49): 34683-34690, the contents of which are expressly incorporated by reference herein).

Compounds of the invention can also be tested for their ability as inhibitors of $LTA_4$-h hydrolase in the whole blood assay using human, mouse, rat or dog whole blood (see Penning, T. D. et al., J. Med. Chem. (2000), 43(4): 721-735 for a description of a human whole blood assay and a mouse whole blood assay, the contents of which are expressly incorporated herein).

A hallmark of inflammation is the adhesion and transmigration across endothelium of neutrophils, eosinophils and other inflammatory cells. A similar process is observed for the migration of cells across polarized epithelial cells that occur in the lung, gastrointestinal tract and other organs. Cell culture models of these processes are available and can be used to show the ability of the compounds of the invention to inhibit the transmigration of human neutrophils across human endothelial cells and epithelial cells, including the human intestinal epithelial cell line $T_{84}$. Accordingly, one of ordinary skill in the art can test the compounds of the invention for their ability to inhibit the transmigration of human neutrophils and eosinophils across human endothelial cells and epithelial cells by performing assays similar to those described in Colgan, S. P., et al., J. Clin. Invest 1993, Vol. 92, No. 1, pp. 75-82, and Serhan, C. N., et al., Biochemistry 1995, Vol. 34, No. 44, pp. 14609-14615.

The air pouch model and/or the mouse zymosan-induced peritonitis model can be used to evaluate the in vivo efficacy of the compounds of the invention in treating an inflammatory response. These are acute experimental models of inflammation characterized by infiltration of inflammatory cells into a localized area. See, for example, the in vivo assays described in Ajuebor, M. N., et al., Immunology 1998, Vol. 95, pp. 625-630; Gronert, K., et al., Am. J. Pathol. 2001, Vol. 158, pp. 3-9; Pouliot, M., et al., Biochemistry 2000, Vol. 39. pp. 4761-4768; Clish, C. B., et al., Proc. Natl. Acad. Sci. U.S.A. 1999, Vol. 96, pp. 8247-8252; Hachicha, M., et al., J. Exp. Med. 1999, Vol. 189, pp. 1923-30.

Animal models (i.e., in vivo assays) can also be utilized to determine the efficacy of the compounds of the invention in treating asthma and related disorders of the pulmonary and respiratory tract, including, but not limited to, asthma. See, for example, the assays described in De Sanctis, G. T. et al., Journal of Clinical Investigation 1999, Vol. 103, pp. 507-515, and Campbell, E. M., et al., J. Immunol. 1998, Vol. 161, No. 12, pp. 7047-7053.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see The Science and Practice of Pharmacy, 20.sup.third Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention can be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition can be in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example a gelatin capsule, it may contain, in addition to materials of the above type, a liquid carrier such as polyethylene glycol or oil.

The pharmaceutical composition can be in the form of a liquid, for example, an elixir, syrup, solution, emulsion or suspension. The liquid can be for oral administration or for delivery by injection, as two examples. When intended for oral administration, a composition can contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether solutions, suspensions or other like form, can include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention can be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention can be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention can include various materials, which modify the physical form of a solid or liquid dosage unit. For example, the composition can include materials that form a coating shell around the active ingredients. The materials that form the coating shell are typically inert, and may be selected from, for example, sugar, shellac, and other enteric coating agents. Alternatively, the active ingredients can be encased in a gelatin capsule.

The pharmaceutical composition of the invention in solid or liquid form can include an agent that binds to the compound of the invention and thereby assists in the delivery of the compound. Suitable agents that may act in this capacity include a monoclonal or polyclonal antibody, a protein or a liposome.

The pharmaceutical composition of the invention can consist of dosage units that can be administered as an aerosol. The term aerosol is used to denote a variety of systems ranging from those of colloidal nature to systems consisting of pressurized packages. Delivery can be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention cam be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors and can be determined routinely by one of ordinary skill in the art. Generally, a therapeutically effective daily dose is (for a 70 kg mammal) from about 0.001 mg/kg (i.e., 0.7 mg) to about 100 mg/kg (i.e., 7.0 gm); preferably a therapeutically effective dose is (for a 70 kg mammal) from about 0.01 mg/kg (i.e., 7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent can be administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

The compounds of the invention are inhibitors of $LTA_4$ hydrolase activity and are therefore useful in treating diseases and disorders which are ameliorated by the inhibition of LTA4 hydrolase activity. Such diseases and conditions include inflammatory and autoimmune disorders and pulmonary and respiratory tract inflammation.

Accordingly, the compounds are useful in the treatment of the following diseases or disorders in mammals, particularly humans: acute or chronic inflammation, anaphylactic reactions, allergic reactions, allergic contact dermatitis, allergic rhinitis, chemical and non-specific irritant contact dermatitis, urticaria, atopic dermatitis, psoriasis, fistulas associated with Crohn's disease, pouchitis, septic or endotoxic shock, hemorrhagic shock, shock-like syndromes, capillary leak syndromes induced by immunotherapy of cancer, acute respiratory distress syndrome, cystic fibrosis, traumatic shock, immune- and pathogen-induced pneumonias, immune complex-mediated pulmonary injury and chronic obstructive pulmonary disease, inflammatory bowel diseases (including ulcerative colitis, Crohn's disease and post-surgical trauma), gastrointestinal ulcers, diseases associated with ischemia-reperfusion injury (including acute myocardial ischemia and infarction, acute renal failure, ischemic bowel disease and acute hemorrhagic or ischemic stroke), immune-complex-mediated glomerulonephritis, autoimmune diseases (including insulin-dependent diabetes mellitus, multiple sclerosis, rheumatoid arthritis, osteoarthritis and systemic lupus erythematosus), acute and chronic organ transplant rejection, transplant arteriosclerosis and fibrosis, cardiovascular disorders (including hypertension, atherosclerosis, aneurysm, critical leg ischemia, peripheral arterial occlusive disease and Reynaud's syndrome), complications of diabetes (including diabetic nephropathy, neuropathy and retinopathy), ocular disorders (including macular degeneration and glaucoma), neurodegenerative disorders (including delayed neurodegeneration in stroke, Alzheimer's disease, Parkinson's disease, encephalitis and HIV dementia), inflammatory and neuropathic pain including arthritic pain, periodontal disease including gingivitis, ear infections, migraine, benign prostatic hyperplasia, and cancers (including, but not limited to, leukemias and lymphomas, prostate cancer, breast cancer, lung cancer, malignant melanoma, renal carcinoma, head and neck tumors and colorectal cancer).

The compounds are also useful in treating folliculitis induced by inhibitors of epidermal growth factor (EGF) or epidermal growth factor receptor (EGFR) kinase used in the treatment of solid tumors. Clinical trials have revealed folliculitis (inflammation of the hair follicle manifested by severe acne-like skin rash on the face, chest and upper back) as a major dose-limiting side effect of such treatments. Such folliculitis is associated with an infiltration of neutrophils suggesting products secreted by activated neutrophils to be the cause of the inflammation. The compounds of the invention inhibit neutrophil or eosinophil-mediated inflammation, and are therefore useful in treating such folliculitis, thereby improving the quality of life of the treated cancer patients but also allowing for the increase of the dosage of the EGF inhibitor or EGFR kinase inhibitor or the extension of the duration of the treatment, resulting in improved efficacy of the desired inhibitor.

The compounds are also useful in the treatment of pulmonary and respiratory inflammation disorders in mammals, particularly humans, including, but not limited to, asthma, chronic bronchitis, bronchiolitis, bronchiolitis obliterans (including such with organizing pneumonia), allergic inflammation of the respiratory tract (including rhinitis and sinusitis), eosinophilic granuloma, pneumonias, pulmonary fibroses, pulmonary manifestations of connective tissue diseases, acute or chronic lung injury, chronic obstructive pulmonary diseases, adult respiratory distress syndrome, and other non-infectious inflammatory disorders of the lung characterized by eosinophil infiltration.

For example, the compounds of the invention are useful in the inhibition of: eosinophil-mediated inflammation of the lung or tissues; neutrophil-mediated inflammation of the lung; lymphocyte-mediated inflammation of the lung; airway hyper-responsiveness; and airway and vascular inflammation.

The compounds are also useful in the treatment of myocardial infarction or susceptibility to myocardial infarction in mammals, particularly humans, transient ischemic attack, transient monocular blindness, stroke or susceptibility of stroke, claudication, peripheral arterial occlusive disease or susceptibility to peripheral arterial occlusive disease, and acute coronary syndrome (such as unstable angina, non-ST-elevation myocardial infarction or ST-elevation myocardial infarction). The compounds are also useful in the methods for reducing the risk of myocardial infarction, stroke or peripheral arterial occlusive disease in mammals and reducing the risk of a second myocardial infarction or stroke.

The compounds are also useful in the treatment of atherosclerosis in mammals, particularly humans who require treatment (such as angioplasty, stents, coronary artery bypass graft) in order to restore blood flow in the arteries (such as in the coronary arteries).

The compounds described herein can also be used in the treatment of neurodegenerative diseases. Non-limiting examples of neurodegenerative diseases that can be treated according to a method of the invention are amyotrophic lateral sclerosis (ALS), Parkinson's disease and Huntington's disease.

The compounds of the invention can be used in the treatment of cancer. In some embodiments, the cancer is a leukemia. Specific exemplary leukemias that can be treated by administering a compound of the invention are Chronic Granulocytic Leukemias, Chronic B-Cell Leukemias and Chronic Myelogenous Leukemias. The invention also encompasses a method of treating a solid tumor in a subject in need thereof. Non-limiting examples of solid tumors that can be treated according to the methods described herein are ovarian, esophageal and hepatocellular tumors.

In certain embodiments, the invention is a method of treating respiratory inflammation in a subject in need thereof comprising administering to said subject a compound of described herein. In one embodiment, the respiratory inflammation is cystic fibrosis.

In yet additional aspects, the invention encompasses a method of treating an inflammatory skin condition. Non-limiting examples of inflammatory skin conditions are atopic dermatitis, acne, psoriasis and eczema.

In some embodiments, the invention is directed to a method of treating a condition selected from the group consisting of cystic fibrosis, idiopathic pulmonary fibrosis, interstitial lung disease associated with systemic sclerosis, atherosclerosis, osteoarthritis, Alzheimer's disease, osteoporosis, and type II diabetes, allergic rhinitis, acne, and gingivitis. Also encompasses is a method of treating an eosinophilic disorder. Exemplary eosinophilic disorders are eosinophilic esophagitis, eosinophilic gastroenteritis, eosinophilic colitis, eosinophilic fasciitis, eosinophilic pneumonia, eosinophilic cystitis, hypereosinophilic syndrome and Churg Strauss Syndrome. In some embodiments, the eosinophilic disorder is eosinophilic esophagitis.

The compounds are also useful in inhibiting the synthesis of leukotriene $B_4$ in both in vitro and in vivo assays.

The invention is illustrated by the following non-limiting examples.

EXEMPLIFICATION

EXAMPLE 1

Preparation of Substituted Anilines

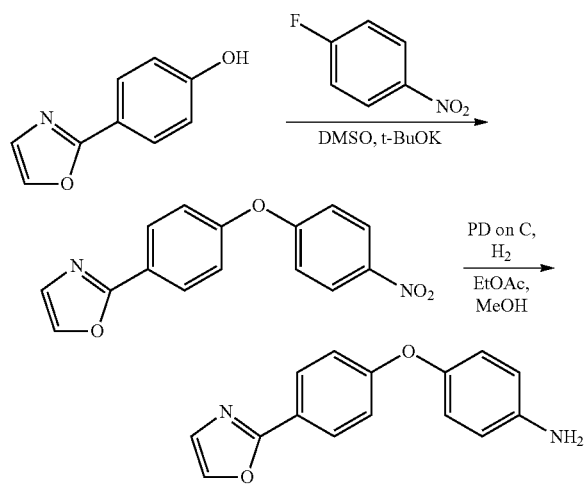

A. A solution of 4-(2-oxazolyl)phenol (10.8 g, 11.2 mmol) in DMSO (9 mL) was stirred as potassium tert-butoxide (1.5 g, 13.4 mmol) and 4-fluoro-nitrobenzene (1.3 mL, 12.3 mmol) were added sequentially. The reaction was stirred for 17 h at ambient temperature. The reaction was poured into a cold aqueous sodium hydroxide solution (1 N). The solid was isolated by filtration to give 2.6 g of 2-[4-(4-nitrophenoxy)phenyl]oxazole.

B. A slurry of 2-[4-(4-nitrophenoxy)phenyl]oxazole (2.6 g, 9.2 mmol) in a mixture of ethyl acetate (20 mL) and methanol (100 mL) was placed under a nitrogen atmosphere before the addition of catalyst palladium (10% on C, 0.65 g). The reaction mixture was placed under a hydrogen atmosphere at atmospheric pressure. After 3 h, the reaction mixture was filtered through a pad of Celite and washed with methanol. The filtrate was concentrated to give the 2.4 g of 4-[4-(2-oxazolyl)phenoxy]benzenamine.

The substituted anilines described below were purchased from Sigma-Aldrich or prepared as described above.

EXAMPLE 2

Preparation of 4-(2,2,3,3,3-pentafluoropropoxy)phenylamine

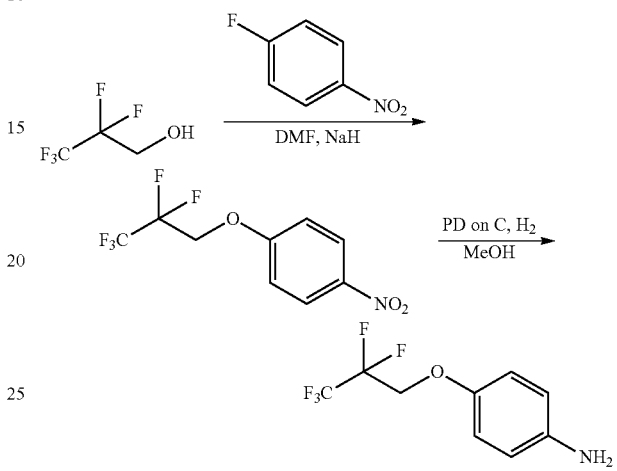

A slurry of sodium hydride (1 g, 24 mmol) in DMF (75 mL) was stirred as 2,2,3,3,3-pentafluoropropanol (2 mL, 20 mmol) was added over 50 min. The reaction mixture was treated with 4-fluoro-l-nitrobenzene (2.1 mL, 20 mmol) and stirred for 16 h. The reaction was quenched with water and extracted with ether. Purification using flash chromatography using a gradient of ethyl acetate in hexane gave 3.7 g of 1-nitro-4-(2,2,3,3,3-pentafluoropropoxy)benzene: $^1$H NMR (CDCl$_3$, 400MHz) δ 8.21 (d, 2H), 6.94 (d, 2H), 4.43 (t, 2H).

A solution of 1-nitro-4-(2,2,3,3,3-pentafluoropropoxy)benzene (3.7 g, 13.7 mmol) in methanol (50 mL) was deoxygenated by bubbling nitrogen through the solution before the addition of 10% Pd/C (0.37 g). The reaction mixture was stirred and placed under a hydrogen atmosphere for 16 h. The reaction was filtered through a pad of Celite and washed with methanol. The filtrates were concentrated to give 3.4 g. Purification using flash chromatography using a gradient of methylene chloride in hexane gave 2.5 g of 4-(2,2,3,3,3-pentafluoropropoxy)phenylamine: $^1$H NMR (CDCl$_3$, 400MHz) δ 6.71 (d, 2H), 6.64 (d, 2H), 4.33 (t, 2H), 3.48 (s, 2H).

EXAMPLE 3

Preparation of Compound 9

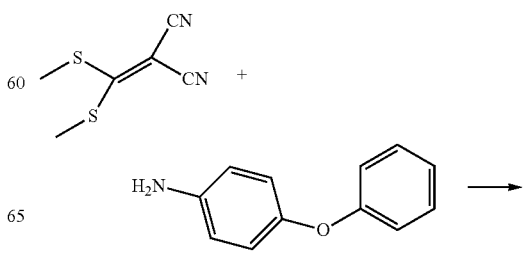

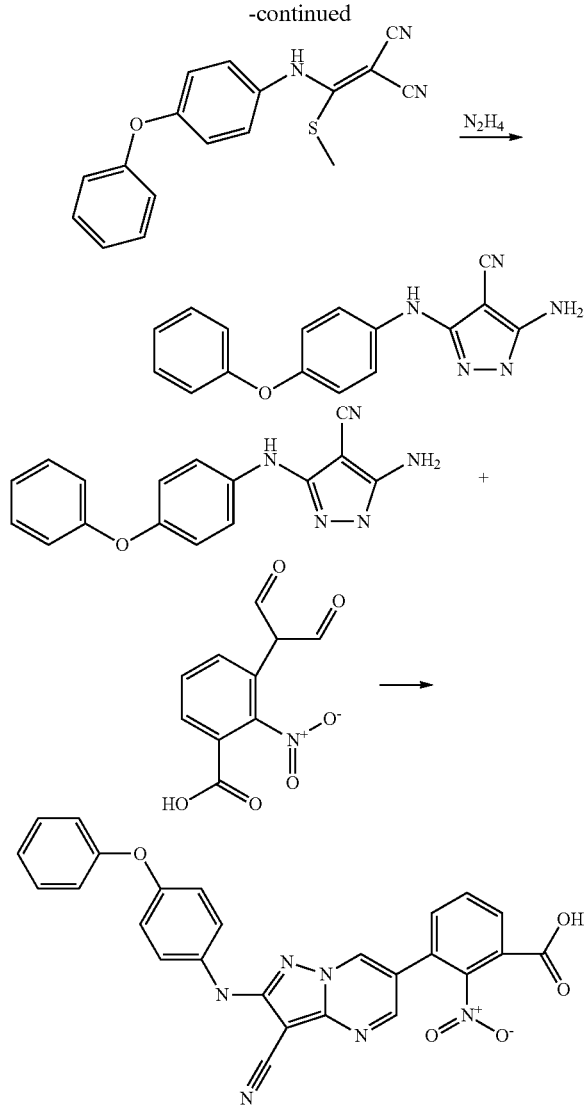

A solution of 2-[Bis-(methylsulfanyl)methylene]malononitrile in absolute ethanol was treated with 4-phenoxyaniline and the mixture was heated at reflux until all starting material was consumed. Solvent was removed under reduced pressure to yield the desired 2-[(4-phenoxyphenylamino)-2-methylsulfanylmethylene]malononitrile.

A solution of desired 2-[(4-phenoxyphenylamino)-2-methylsulfanylmethylene]malononitrile in absolute ethanol was treated with hydrazine and the reaction was heated at reflux until the starting material was consumed. The reaction was allowed to cool and solvent removed under reduced pressure to give the desired 1H-3-amino-4-cyano-5-(4-phenoxyphenylamino)pyrazole.

A mixture of 1H-3-amino-4-cyano-5-(4-phenoxyphenylamino)pyrazole and 2-(2-nitro-3-hydroxycarboxyphenyl)-malondialdehyde were combined in a alcohol solvent and heated unitl starting material had been consumed. Solvent was removed and desired 2-(4-phenoxyphenylamino)-3-cyano-6-(2-nitro-3-hydroxycarboxyphenyl)pyrazolo[1,5-a]pyrimidine was isolated.

EXAMPLE 4

Biological Activity

Table 2 below shows the $IC_{50}$ values for peptidase, hydrolase and whole blood assay (WBA) activity for exemplary compounds encompassed by the invention. The whole blood and aminopeptidase assays were performed as described in Penning et al., J. Med. Chem. 2000, 43, 721-735, and Rudberg et al., J. Biol. Chem. Vol. 279, No. 26, Issue of June 25, pp. 27376-27382, 2004, the contents of each of which are expressly incorporated by reference herein. The hydrolase assay was performed as described in U.S. Pat. No. 7,737,145, the contents of which are expressly incorporated herein.

TABLE 2

| Compound No. | X = | Y = | $IC_{50}$ Peptidase (nM) | $IC_{50}$ Hydrolase (nM or % inhibition) | $IC_{50}$ WBA (nM) |
|---|---|---|---|---|---|
| 1 | PhO | $NH_2$ | 280 (N3) | 1500 (N3) | >8800 (N2) |
| 2 | PhO | $NO_2$ (2-nitro-4-SO2Me-phenyl) | 260 (N2) | 3700 | >7200 (N2) |

TABLE 2-continued

Structure: 4-X-phenyl-NH attached to pyrazolo[1,5-a]pyrimidine bearing CN at 3-position and Y at 6-position.

| Compound No. | X = | Y = | IC$_{50}$ Peptidase (nM) | IC$_{50}$ Hydrolase (nM or % inhibition) | IC$_{50}$ WBA (nM) |
|---|---|---|---|---|---|
| 3 | PhO | 3-methyl-4-nitrobenzoic acid | 430 (N3) | 39% inhibition at 3 uM | >10000 (N2) |
| 4 | PhO | 2-hydroxy-3-acetyl-5-nitrophenyl | 1700 (N2) | 48% inhibition at 3 uM (N2) | |
| 5 | PhO | 2-hydroxy-acetophenone | 90 (N2)<br>20 (N2) | 1400 (N3)<br>490 (N2) | 4900 (N2)<br>3000 (N2) |
| 6 | PhO | 3,5-dichloro-2-hydroxy-acetophenone | 960 (N2) | 15% @ 3 uM (N2) | |
| 7 | PhO | 5-chloro-2-hydroxy-acetophenone | 30 (N3)<br>10 (n2) | 1600 (N2)<br>2900 | 4600 (N2)<br>3000 (N2) |
| 8 | OPh | 2-hydroxy-acetophenone | 0% inhibition at 3 uM | | |
| 9 | —OPh | 2-nitro-3-methylbenzoic acid | 3.3 | 20% inhibition at 1 uM | |
| 10 | —OPh | 3-nitro-4-methylbenzoic acid | 120 (n = 2) | 20% inhibition at 1 uM | |

TABLE 2-continued

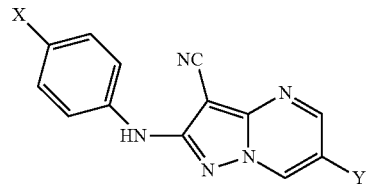

| Compound No. | X = | Y = | IC$_{50}$ Peptidase (nM) | IC$_{50}$ Hydrolase (nM or % inhibition) | IC$_{50}$ WBA (nM) |
| --- | --- | --- | --- | --- | --- |
| 11 | —OPh | 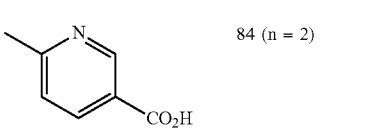 | 270 (n = 2) | | |
| 12 | —OPh | 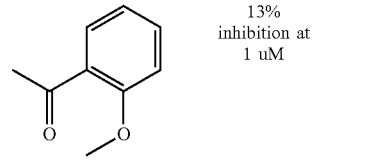 | 84 (n = 2) | | |
| 13 | —OPh | 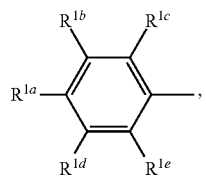 | 13% inhibition at 1 uM | | |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having the Formula (I):

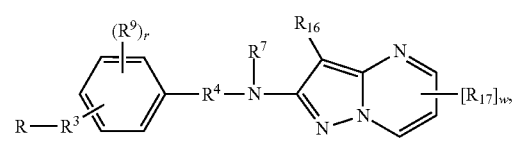

or a pharmaceutically acceptable salt thereof, wherein:
R is the group:

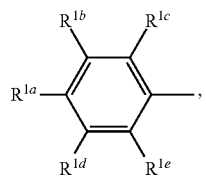

r is 0 to 4;
$R^{1a}$, $R^{1b}$, $R^{1c}$, $R^{1d}$ and $R^{1e}$ are each independently hydrogen, $OR^{10}$, $C(O)OR^{10}$, $C(O)R^{10}$, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, or optionally substituted heterocyclyl;

$R^3$ is —O—;

$R^4$ is a direct bond, —O—$R^{12a}$, an optionally substituted straight or branched $C_1$ to $C_{12}$ alkylene chain, an optionally substituted straight or branched $C_2$ to $C_{12}$ alkenylene chain, or an optionally substituted straight or branched $C_3$ to $C_{12}$ alkynylene chain;

$R^7$ is selected from the group consisting of hydrogen, $OR^{10}$, $C(O)R^{10}$, $C(O)OR^{10}$, $C(O)$—$R^{13}$—$N(R^{10})R^{11}$, $N(R^{10})C(O)N(R^{10})R^{11}$, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, optionally substituted aryl, optionally substituted heteroaryl, and optionally substituted heterocyclyl;

each $R^9$ is independently —$OR^{10}$, optionally substituted $C_1$-$C_{12}$ alkyl, optionally substituted $C_2$-$C_{12}$ alkenyl, optionally substituted $C_2$-$C_{12}$ alkynyl, halo, aryl, or heteroaryl;

each $R^{10}$ and $R^{11}$ is independently selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, optionally substituted aryl, optionally substituted heteroaryl, and optionally substituted heterocyclyl;

or $R^{10}$ and $R^{11}$, together with the nitrogen to which they are attached, form an optionally substituted N-heterocyclyl or an optionally substituted N-heteroaryl;

$R^{12a}$ is an optionally substituted straight or branched $C_1$ to $C_{12}$ alkylene chain, an optionally substituted straight or branched $C_2$ to $C_{12}$ alkenylene chain, or an optionally substituted straight or branched $C_3$ to $C_{12}$ alkynylene chain;

each $R^{13}$ is independently a direct bond, an optionally substituted straight or branched $C_1$ to $C_{12}$ alkylene chain, an optionally substituted straight or branched $C_2$ to $C_{12}$ alkenylene chain, or an optionally substituted straight or branched $C_3$ to $C_{12}$ alkynylene chain; and $R^{16}$ is selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, optionally substituted heterocyclyl, $OR^{10}$, $C(O)R^{10}$, $C(O)OR^{10}$, $C(O)$—$R^{13}$—$N(R^{10})R^{11}$, $N(R^{10})C(O)N(R^{10})R^{11}$, $NR^{10}R^{11}$, and $N(R^{10})C(O)R^{10}$;

each $R^{17}$ is independently selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, optionally substituted heterocyclyl, $OR^{10}$, $NO_2$, $S(O)_jR^{10}$, $S(O)_jNR^{10}R^{11}$, $C(O)R^{10}$, $C(O)OR^{10}$, $C(O)$—$R^{13}$—$N(R^{10})R^{11}$, $N(R^{10})C(O)N(R^{10})R^{11}$, $NR^{10}R^{11}$, and $N(R^{10})C(O)R^{10}$;

wherein w is an integer from 1 to 3; and j is 0, 1, or 2.

2. The compound of claim 1, wherein $R^{16}$ is cyano; or a pharmaceutically acceptable salt thereof.

3. The compound of claim 1, wherein w is 1 and $R^{17}$ is selected from the group consisting of optionally substituted aryl, optionally substituted heteroaryl, and $C(O)R_{20}$, wherein $R_{20}$ is selected from the group consisting of optionally substituted aryl and optionally substituted heteroaryl; or a pharmaceutically acceptable salt thereof.

4. The compound of claim 1, wherein the compound has the Formula (Ia):

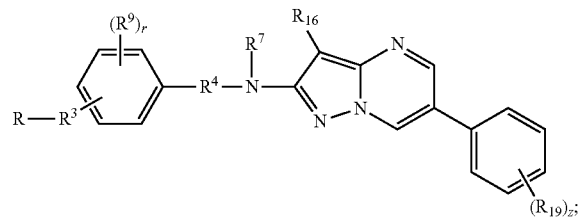

(Ia)

or a pharmaceutically acceptable salt thereof;
wherein each $R^{19}$ is independently selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, optionally substituted heterocyclyl, $OR^{10}$, $NO_2$, $S(O)_jR^{10}$, $S(O)_jNR^{10}R^{11}$; $C(O)R^{10}$, $C(O)OR^{10}$, $C(O)$—$R^{13}$—$N(R^{10})R^{11}$, $N(R^{10})C(O)N(R^{10})R^{11}$, $NR^{10}R^{11}$, and $N(R^{10})C(O)R^{10}$;

wherein z is an integer from 1 to 5.

5. The compound of claim 4, wherein z is 1 or 2, and each $R^{19}$ is independently selected from the group consisting of hydrogen, hydroxyl, halo, optionally substituted $C_1$-$C_4$ alkyl, $C(O)R^{10}$, $C(O)OR^{10}$, $NO_2$, $S(O)_jR^{10}$ and $S(O)_jNR^{10}R^{11}$; or a pharmaceutically acceptable salt thereof.

6. The compound of claim 4, wherein $R^{16}$ is cyano; or a pharmaceutically acceptable salt thereof.

7. The compound of claim 1, wherein the compound has the Formula (Ib):

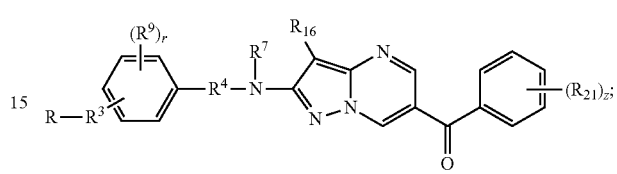

or a pharmaceutically acceptable salt thereof;
wherein each $R^{21}$ is independently selected from the group consisting of hydrogen, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, optionally substituted heterocyclyl, $OR^{10}$, $NO_2$, $S(O)_jR^{10}$, $S(O)_jNR^{10}R^{11}$; $C(O)R^{10}$, $C(O)OR^{10}$, $C(O)$—$R^{13}$—$N(R^{10})R^{11}$, $N(R^{10})C(O)N(R^{10})R^{11}$, $NR^{10}R^{11}$, and $N(R^{10})C(O)R^{10}$;

wherein z is an integer from 1 to 5.

8. The compound of claim 7, wherein z is 1 or 2, and each $R^{21}$ is independently selected from the group consisting of hydrogen, hydroxyl, halo, optionally substituted $C_1$-$C_4$ alkyl, $C(O)R^{10}$, $C(O)OR^{10}$, $NO_2$, $S(O)_jR^{10}$ and $S(O)_jNR^{10}R^{11}$; or a pharmaceutically acceptable salt thereof.

9. The compound of claim 8, wherein each $R^{21}$ is independently selected from the group consisting of hydrogen, hydroxyl and halo, or a pharmaceutically acceptable salt thereof.

10. The compound of claim 3, wherein $R^{17}$ is optionally substituted heteroaryl; or a pharmaceutically acceptable salt thereof.

11. The compound of claim 10, wherein $R^{17}$ is an optionally substituted heteroaryl containing one or more ring nitrogen atoms; or a pharmaceutically acceptable salt thereof.

12. The compound of claim 11, wherein $R^{17}$ is optionally substituted pyridyl; or a pharmaceutically acceptable salt thereof.

13. The compound of claim 7, wherein $R^{16}$ is cyano; or a pharmaceutically acceptable salt thereof.

14. The compound of claim 1, wherein $R^{1a}$ is selected from the group consisting of hydrogen, $C(O)OR^{10}$, $C(O)R^{10}$, optionally substituted $C_1$-$C_{12}$ alkyl, optionally substituted $C_2$-$C_{12}$ alkenyl, optionally substituted $C_2$-$C_{12}$ alkynyl, optionally substituted $C_3$-$C_{15}$ cycloalkyl, optionally substituted $C_3$-$C_{15}$ cycloalkenyl, halo, cyano, optionally substituted aryl, optionally substituted heteroaryl, and optionally substituted heterocyclyl; or a pharmaceutically acceptable salt thereof.

15. The compound of claim 14, wherein $R^{1a}$ is selected from the group consisting of hydrogen, $C(O)OR^{10}$, $C(O)R^{10}$, optionally substituted alkyl, halo, optionally substituted phenyl, optionally substituted furanyl, optionally substituted thienyl, optionally substituted thiazolyl, and optionally substituted oxazolyl; and wherein $R^{1b}$, $R^{1c}$, $R^{1d}$ and $R^{1e}$ are each hydrogen, or a pharmaceutically acceptable salt thereof.

16. The compound of claim 1, wherein $R^4$ is a direct bond, an optionally substituted methylene or an optionally substituted ethylene, or a pharmaceutically acceptable salt thereof.

17. The compound of claim 16, wherein $R^4$ is methylene, or a pharmaceutically acceptable salt thereof.

18. The compound of claim 1, wherein $R^7$ is hydrogen or optionally substituted $C_1$-$C_6$ alkyl, or a pharmaceutically acceptable salt thereof.

19. The compound of claim 18, wherein $R^7$ is hydrogen, $C_1$-$C_6$ alkyl optionally substituted with $OR^{10}$, or $C_1$-$C_6$ alkyl optionally substituted with $NR^{10}R^{11}$, or a pharmaceutically acceptable salt thereof.

20. The compound of claim 19, wherein $R^7$ is hydrogen or methyl, or a pharmaceutically acceptable salt thereof.

21. The compound of claim 1 selected from the following compounds, or a pharmaceutically acceptable salt thereof:

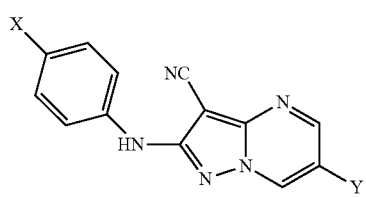

| X | Y |
|---|---|
| PhO | NH$_2$ |
| PhO | 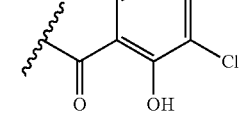 |
| PhO |  |
| PhO | 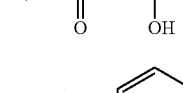 |
| PhO | 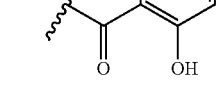 |
| PhO | 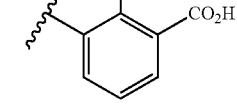 |
| PhO | 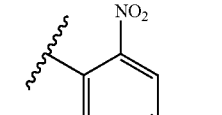 |
| OPh | 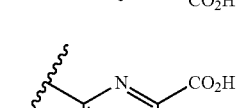 |
| —OPh | 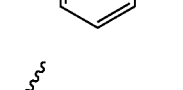 |
| —OPh | |
| —OPh | |
| —OPh | |
| —OPh | |

22. A pharmaceutical composition comprising a pharmaceutically acceptable excipient and a compound of claim 1, or a pharmaceutically acceptable salt thereof.

23. The compound of claim 4, wherein r is 0 and $R^4$ is a direct bond; or a pharmaceutically acceptable salt thereof.

24. The compound of claim 7, wherein r is 0 and $R^4$ is a direct bond; or a pharmaceutically acceptable salt thereof.

25. The compound of claim 10, wherein r is 0 and $R^4$ is a direct bond; or a pharmaceutically acceptable salt thereof.

26. The compound of claim 18, wherein r is 0 and $R^4$ is a direct bond; or a pharmaceutically acceptable salt thereof.

* * * * *